United States Patent

Sun et al.

(10) Patent No.: US 9,383,474 B1
(45) Date of Patent: Jul. 5, 2016

(54) SYSTEM AND METHOD FOR DETECTING FILM LAYER

(71) Applicants: BOE TECHNOLOGY GROUP CO., LTD., Beijing (CN); BEIJING BOE DISPLAY TECHNOLOGY CO., LTD., Beijing (CN)

(72) Inventors: Zhiyi Sun, Beijing (CN); Rongji Ma, Beijing (CN); Ran Zhang, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 14/739,752

(22) Filed: Jun. 15, 2015

(30) Foreign Application Priority Data

Mar. 30, 2015 (CN) .......................... 2015 1 0145947

(51) Int. Cl.
 *G01J 5/00* (2006.01)
 *G01V 8/12* (2006.01)
(52) U.S. Cl.
 CPC ....................... *G01V 8/12* (2013.01)
(58) Field of Classification Search
 CPC .............................. G01N 2223/633
 See application file for complete search history.

(56) References Cited

U.S. PATENT DOCUMENTS

2010/0219400 A1* 9/2010 Arakane ............ H01L 51/0054
257/40

FOREIGN PATENT DOCUMENTS

| JP | 03059441 A | * | 3/1991 |
| JP | 04141583 A | * | 5/1992 |
| JP | 07169808 A | * | 7/1995 |
| JP | 2006047143 A | * | 2/2006 |

* cited by examiner

*Primary Examiner* — Kiho Kim
(74) *Attorney, Agent, or Firm* — Harness, Dickey & Pierce, P.L.C.

(57) ABSTRACT

A system includes a linear light source configured to emit a detection light beam to the light sensor, a light sensor configured to receive the detection light beam and convert it into a photo sensitive signal, the detection light beam being capable of passing through the substrate; a movement device configured to move the substrate through a detection region, the detection region being a region at which the detection light beam intersects a plane where the substrate is located when the substrate is moved by the movement device; and a processing unit configured to determine whether or not the film layer meets a predetermined requirement by determining whether or not an intensity of the photo sensitive signal generated during a period of time where the substrate is moved through the detection region is within a predetermined range.

19 Claims, 1 Drawing Sheet

SYSTEM AND METHOD FOR DETECTING FILM LAYER

CROSS-REFERENCE TO RELATED APPLICATION

The present application claims a priority of the Chinese patent application No. 201510145947.6 filed on Mar. 30, 2015, which is incorporated herein by reference in its entirety.

TECHNICAL FIELD

The present disclosure relates to the field of film layer detection, in particular to a system and a method for detecting a film layer.

BACKGROUND

An indium tin oxide (ITO) film is an indispensible component of an electrode in a liquid crystal display or a transparent metal film for electrostatic shielding. The ITO film is of a very small thickness and has high visible-light transmittance, so it is difficult for human's eyes to determine whether the ITO film exists or not.

In an existing detection method, whether the ITO film exists or not is mainly detected by testing an area resistance of a substrate. However, it takes a long period of time for a traditional device to test the area resistance of the substrate, and an area to be detected is relatively small, so it is impossible to perform the detection rapidly.

SUMMARY

An object of the present disclosure is to provide a system and a method for detecting a film layer, so as to accelerate a detection speed.

In one aspect, the present disclosure provides in one embodiment a system for detecting a film layer, which is arranged on a substrate. The substrate includes a rectangular base substrate, and the film layer covers the base substrate. The system includes:

a linear light source and a light sensor, the linear light source being configured to emit a detection light beam to the light sensor, the light sensor being configured to receive the detection light beam and convert it into a photo sensitive signal, the detection light beam being capable of passing through the substrate;

a movement device configured to move the substrate through a detection region, the detection region being a region at which the detection light beam intersects a plane where the substrate is located when the substrate is moved by the movement device; and a processing unit configured to determine whether or not the film layer meets a predetermined requirement by determining whether or not an intensity of the photo sensitive signal generated during a period of time where the substrate is moved through the detection region is within a predetermined range.

Alternatively, during the period of time where the substrate is moved through the detection region, when the intensity a of the photo sensitive signal at the detection region always meets $A \le \alpha \le B$, the processing unit determines that the film layer meets the predetermined requirement. A represents an intensity of a photo sensitive signal generated when the detection light beam passes through a substrate where a film layer is of a maximum thickness within a predetermined range and distributed evenly, and B represents an intensity of a photo sensitive signal generated when the detection light beam passes through a substrate where a film layer is of a minimum thickness within the predetermined range and distributed evenly. When $\alpha < A$ or $\alpha > B$, the processing unit determines that the film layer does not meet the predetermined requirement.

Alternatively, when $\alpha < A$, the processing unit determines that the thickness of the film layer is of a value greater than the maximum thickness within the predetermined range. When $B < \alpha < C$, the processing unit determines that the thickness of the film layer is a value less than the minimum thickness within the predetermined range. C represents an intensity of a photo sensitive signal generated when the detection light beam passes through a base substrate where no film layer is arranged. When $\alpha \ge C$, the processing unit determines that the base substrate includes a region where no film layer is arranged.

Alternatively, the light sensor is of a length greater than or equal to the linear light source.

Alternatively, the movement device is located between the linear light source and the light sensor.

Alternatively, the system further includes a sensing device configured to sense whether or not a front end of the substrate has reached the detection region and whether or not a rear end of the substrate has left the detection region, and transmit a sensing signal to the processing unit. The processing unit determines whether or not the film layer meets the predetermined requirement in accordance with the photo sensitive signal during a period of time from the time when the front end of the substrate has reached the detection region to the time when the rear end of the substrate has left the detection region.

Alternatively, the system further includes a collection device connected to the light sensor and the processing unit, and configured to, during the period of time where the substrate is moved through the detection region, collect the photo sensitive signals at a regular time interval and transmit the photo sensitive signals to the processing unit.

Alternatively, when the base substrate is made of inorganic glass and the film layer is made of ITO, the detection light beam from the linear light source is of a wavelength of 100 nm to 280 nm, or 780 nm to 2526 nm.

Alternatively, a side of the base substrate is perpendicular to a movement direction of the movement device and has a length less than or equal to the linear light source.

In another aspect, the present disclosure provides in one embodiment a method for detecting a film layer, including steps of:

emitting, by a linear light source, a detection light beam to a light sensor, and receiving, by the light sensor, the detection light beam and converting into a photo sensitive signal;

moving, by a movement device, the substrate through a detection region, wherein a side of a base substrate of the substrate is perpendicular to a movement direction of the movement device and has a length less than or equal to the linear light source; and determining, by a processing unit, whether or not the film layer meets a predetermined requirement by determining whether or not an intensity of the photo sensitive signal generated during a period of time where the substrate is moved through the detection region is within a predetermined range.

Alternatively, during the period of time where the substrate is moved through the detection region, when the intensity a of the photo sensitive signal at the detection region always meets $A \le \alpha \le B$, the processing unit determines that the film layer meets the predetermined requirement. A represents an intensity of a photo sensitive signal generated when the detection light beam passes through a substrate where a film layer is of a maximum thickness within a predetermined range and distributed evenly, and B represents an intensity of a photo sensitive signal generated when the detection light beam passes through a substrate where a film layer is of a minimum thickness within the predetermined range and distributed evenly. When α<A or α>B, the processing unit determines that the film layer does not meet the predetermined requirement.

Alternatively, when α<A, the processing unit determines that the thickness of the film layer is of a value greater than the maximum thickness within the predetermined range. When B<α<C, the processing unit determines that the thickness of the film layer is a value less than the minimum thickness within the predetermined range. C represents an intensity of a photo sensitive signal generated when the detection light beam passes through a base substrate where no film layer is arranged. When α≥C, the processing unit determines that the base substrate includes a region where no film layer is arranged.

According to the system and method in the embodiments of the present disclosure, the detection light beam capable of passing through the substrate is emitted by the linear light source to the light sensor, and the substrate is moved by the movement device through the detection region. During the period of time where the substrate is moved through the detection, the light sensor receives the detection light beam passing through the substrate and converts it into the photo sensitive signal. The processing unit determines whether or not the film layer of the substrate meets the predetermined requirement by determining whether or not the intensity of the photo sensitive signal is within the predetermined range. As a result, it is able to rapidly detect the film layer of the substrate through a simple structure and a simple method, thereby to accelerate the detection speed as compared with the related art.

DETAILED DESCRIPTION

The present disclosure will be described hereinafter in a clear and complete manner in conjunction with the drawings and embodiments. Obviously, the following embodiments are merely a part of, rather than all of, the embodiments of the present disclosure, and based on these embodiments, a person skilled in the art may, without any creative efforts, obtain the other embodiments, which also fall within the scope of the present disclosure.

Figure 1:
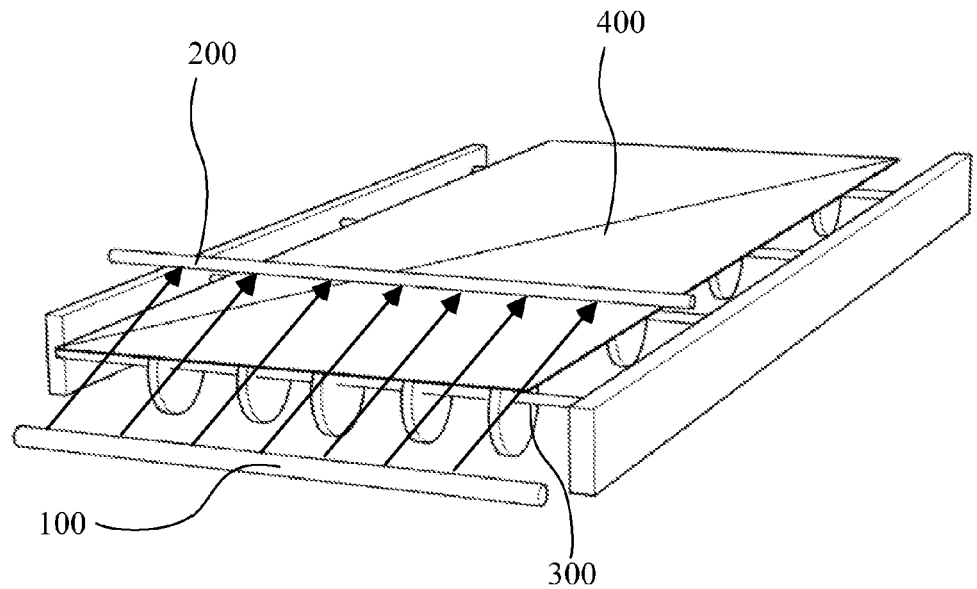
FIG. 1 is a schematic view showing a detection system according to one embodiment of the present disclosure.

Unless otherwise defined, any technical or scientific term used herein shall have the common meaning understood by a person of ordinary skills Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too The present disclosure provides in one embodiment a system for detecting a film layer, which is arranged on a substrate. The substrate includes a rectangular base substrate, and the film layer covers the base substrate. As shown in FIG. 1, the system includes:

a linear light source 100 and a light sensor 200, the linear light source 100 being configured to emit a detection light beam to the light sensor 200, the light sensor 200 being configured to receive the detection light beam and convert it into an photo sensitive signal, the detection light beam being capable of passing through the substrate;

a movement device 300 configured to move the substrate 400 through a detection region, the detection region being a region at which the detection light beam intersects a plane where the substrate is located when the substrate is moved by the movement device; and a processing unit configured to determine whether or not the film layer meets a predetermined requirement by determining whether or not an intensity of the photo sensitive signal generated during a period of time where the substrate 400 is moved through the detection region is within a predetermined range.

Figure 2:
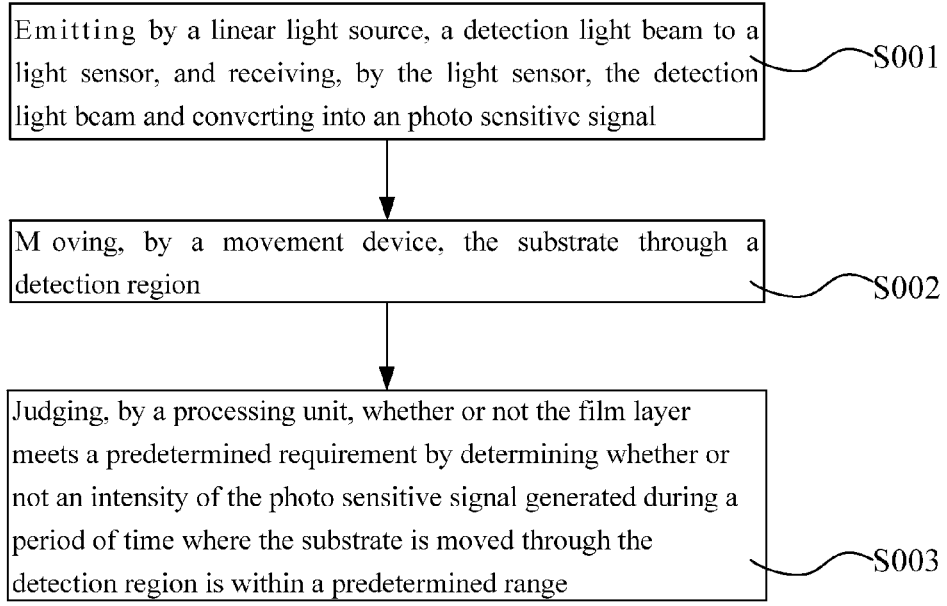
FIG. 2 is a flow chart of a detection method according to one embodiment of the present disclosure.

The present disclosure further provides in one embodiment a method for detecting a film layer. As shown in FIG. 2, the method includes steps of:

Step S001: emitting, by a linear light source, a detection light beam to a light sensor, and receiving, by the light sensor, the detection light beam and converting into an photo sensitive signal;

Step S002: moving, by a movement device, the substrate through a detection region, a side of a base substrate being perpendicular to a movement direction of the movement device and having a length less than or equal to the linear light source; and Step S003: determining, by a processing unit, whether or not the film layer meets a predetermined requirement by determining whether or not an intensity of the photo sensitive signal generated during a period of time where the substrate is moved through the detection region is within a predetermined range.

According to the system and method in the embodiments of the present disclosure, the detection light beam capable of passing through the substrate is emitted by the linear light source to the light sensor, and the substrate is moved by the movement device through the detection region. During the period of time where the substrate is moved through the detection, the light sensor receives the detection light beam passing through the substrate and converts it into the photo sensitive signal. The processing unit determines whether or not the film layer of the substrate meets the predetermined requirement by determining whether or not the intensity of the photo sensitive signal is within the predetermined range. As a result, it is able to rapidly detect the film layer of the substrate through a simple structure and a simple method, thereby to accelerate the detection speed as compared with the related art.

To be specific, during the period of time where the substrate is moved through the detection region, when the intensity a of the photo sensitive signal at the detection region always meets A≤α≤B, the processing unit determines that the film layer meets the predetermined requirement. A represents an intensity of an photo sensitive signal generated when the detection light beam passes through a substrate where a film layer is of a maximum thickness within a predetermined range and distributed evenly, and B represents an intensity of an photo sensitive signal generated when the detection light beam passes through a substrate where a film layer is of a minimum thickness within the predetermined range and distributed evenly. When $\alpha<A$ or $\alpha>B$, the processing unit determines that the film layer does not meet the predetermined requirement.

In this way, it is able to detect the film layer of the substrate rapidly.

Prior to detecting the substrate with a certain specification, it is required to set the predetermined range, i.e., to find the values of A and B. To be specific, it is required to find at first a standard substrate where a film layer is of a maximum thickness within a predetermined range and distributed evenly. Next, the detection light beam is emitted by the linear light source to the light sensor. Then, the standard substrate is placed on the movement device, and an intensity of an photo sensitive signal generated when the detection light beams passes through the standard substrate is obtained by the light sensor, and this intensity is just the value of A. The value of B may be obtained in a similar manner.

Further, when the film layer does not meet the predetermined requirement, the following situations may be included. When $\alpha<A$, the processing unit determines that the thickness of the film layer is of a value greater than the maximum thickness within the predetermined range. When $B<\alpha<C$, the processing unit determines that the thickness of the film layer is a value less than the minimum thickness within the predetermined range. C represents an intensity of an photo sensitive signal generated when the detection light beam passes through a base substrate where no film layer is arranged. When $\alpha \geq C$, the processing unit determines that the base substrate includes a region where no film layer is arranged.

To be specific, as shown in FIG. 1, the light sensor is of a length greater than or equal to the linear light source. The length of the linear light source determines a width of the detection light beams, and thereby determines a width of the detection region. When the length of the light sensor is greater than or equal to that of the linear light source, i.e., the width of the detection region, it is able to ensure that all the detection light beams passing through the detection region can be received by the light sensor, thereby to ensure the accuracy of the photo sensitive signal generated by the light sensor.

To be specific, as shown in FIG. 1, the movement device 300 is arranged between the linear light source 100 and the light sensor 200. In this way, it is able to simplify the arrangement of the movement device, thereby to simplify the structure of the detection system.

Further, the system may further include a sensing device configured to sense whether or not a front end of the substrate has reached the detection region and whether or not a rear end of the substrate has left the detection region, and transmit a sensing signal to the processing unit. The processing unit determines whether or not the film layer meets the predetermined requirement in accordance with the photo sensitive signal during a period of time from the time when the front end of the substrate has reached the detection region to the time when the rear end of the substrate has left the detection region.

The sensing device cooperates with the processing unit, so as to determine the period of time where the substrate is moved through the detection region, thereby to facilitate the detection on the film layer of the substrate through the processing unit.

Further, the detection system further includes a collection device connected to the light sensor and the processing unit, and configured to, during the period of time where the substrate is moved through the detection region, collect the photo sensitive signals at a regular time interval and transmit the photo sensitive signals to the processing unit.

The time interval for the collection and the movement speed of the substrate determine the number of the photo sensitive signals collected during the period of time where the substrate is moved through the detection region. The more the collected photo sensitive signals, the more accurate the detection on the film layer of the substrate.

To be specific, when the base substrate of the substrate is made of inorganic glass and the film layer is made of ITO, the detection light beam from the linear light source is of a wavelength of 100 nm to 280 nm, or 780 nm to 2526 nm, so as to ensure the detection light beam can pass through the substrate.

The above are merely the preferred embodiments of the present disclosure. It should be appreciated that, a person skilled in the art may make further modifications and improvements without departing from the spirit of the present disclosure. If these modifications and improvements fall within the scope of the appended claims and the equivalents thereof, the present disclosure also intends to include these modifications and improvements.

What is claimed is:

1. A system for detecting a film layer, which is arranged on a substrate, the substrate comprising a rectangular base substrate, the film layer covering the base substrate, the system comprising:
   a linear light source and a light sensor, the linear light source being configured to emit a detection light beam to the light sensor, the light sensor being configured to receive the detection light beam and convert it into a photo sensitive signal, the detection light beam being capable of passing through the substrate;
   a movement device, configured to move the substrate through a detection region, the detection region being a region at which the detection light beam intersects a plane where the substrate is located when the substrate is moved by the movement device; and
   a processing unit, configured to determine whether or not the film layer meets a predetermined requirement by determining whether or not an intensity of the photo sensitive signal generated during a period of time where the substrate is moved through the detection region is within a predetermined range;
   wherein during the period of time where the substrate is moved through the detection region,
   when the intensity $\alpha$ of the photo sensitive signal at the detection region always meets $A \leq \alpha \leq B$, the processing unit determines that the film layer meets the predetermined requirement, wherein A represents an intensity of a photo sensitive signal generated when the detection light beam passes through a substrate where a film layer is of a maximum thickness within a predetermined range and distributed evenly, and B represents an intensity of a photo sensitive signal generated when the detection light beam passes through a substrate where a film layer is of a minimum thickness within the predetermined range and distributed evenly; and
   when $\alpha<A$ or $\alpha>B$, the processing unit determines that the film layer does not meet the predetermined requirement.

2. The system according to claim 1, wherein when $\alpha<A$, the processing unit determines that the thickness of the film layer is of a value greater than the maximum thickness within the predetermined range;
   when $B<\alpha<C$, the processing unit determines that the thickness of the film layer is a value less than the minimum thickness within the predetermined range, wherein C represents an intensity of a photo sensitive signal generated when the detection light beam passes through a base substrate where no film layer is arranged; and when $\alpha \geq C$, the processing unit determines that the base substrate includes a region where no film layer is arranged.

3. The system according to claim 2, wherein the light sensor is of a length greater than or equal to the linear light source.

4. The system according to claim 1, wherein the light sensor is of a length greater than or equal to the linear light source.

5. The system according to claim 1, wherein the movement device is located between the linear light source and the light sensor.

6. The system according to claim 1, further comprising a sensing device configured to sense whether or not a front end of the substrate has reached the detection region and whether or not a rear end of the substrate has left the detection region, and transmit a sensing signal to the processing unit, wherein the processing unit determines whether or not the film layer meets the predetermined requirement in accordance with the photo sensitive signal during a period of time from the time when the front end of the substrate has reached the detection region to the time when the rear end of the substrate has left the detection region.

7. The system according to claim 1, further comprising a collection device connected to the light sensor and the processing unit, and configured to, during the period of time where the substrate is moved through the detection region, collect the photo sensitive signals at a regular time interval and transmit the photo sensitive signals to the processing unit.

8. The system according to claim 1, wherein when the base substrate is made of inorganic glass and the film layer is made of indium tin oxide (ITO), the detection light beam from the linear light source is of a wavelength of 100 nm to 280 nm, or 780 nm to 2526 nm.

9. The system according to claim 1, wherein a side of the base substrate is perpendicular to a movement direction of the movement device and has a length less than or equal to the linear light source.

10. A method for detecting a film layer using the system according to claim 1, comprising steps of:

emitting, by a linear light source, a detection light beam to a light sensor, and receiving, by the light sensor, the detection light beam and converting into a photo sensitive signal;

moving, by a movement device, the substrate through a detection region, wherein a side of a base substrate comprised in the substrate is perpendicular to a movement direction of the movement device and has a length less than or equal to the linear light source; and determining, by a processing unit, whether or not the film layer meets a predetermined requirement by determining whether or not an intensity of the photo sensitive signal generated during a period of time where the substrate is moved through the detection region is within a predetermined range;

wherein during the period of time where the substrate is moved through the detection region, when the intensity a of the photo sensitive signal at the detection region always meets $A \leq \alpha \leq B$, the processing unit determines that the film layer meets the predetermined requirement, wherein A represents an intensity of a photo sensitive signal generated when the detection light beam passes through a substrate where a film layer is of a maximum thickness within a predetermined range and distributed evenly, and B represents an intensity of a photo sensitive signal generated when the detection light beam passes through a substrate where a film layer is of a minimum thickness within the predetermined range and distributed evenly; and when $\alpha < A$ or $\alpha > B$, the processing unit determines that the film layer does not meet the predetermined requirement.

11. The method according to claim 10, wherein when $\alpha < A$, the processing unit determines that the thickness of the film layer is of a value greater than the maximum thickness within the predetermined range;

when $B < \alpha < C$, the processing unit determines that the thickness of the film layer is a value less than the minimum thickness within the predetermined range, wherein C represents an intensity of an photo sensitive signal generated when the detection light beam passes through a base substrate where no film layer is arranged; and when $\alpha \geq C$, the processing unit determines that the base substrate includes a region where no film layer is arranged.

12. A system for detecting a film layer, which is arranged on a substrate, the substrate comprising a rectangular base substrate, the film layer covering the base substrate, the system comprising:

a linear light source and a light sensor, the linear light source being configured to emit a detection light beam to the light sensor, the light sensor being configured to receive the detection light beam and convert it into a photo sensitive signal, the detection light beam being capable of passing through the substrate;

a movement device, configured to move the substrate through a detection region, the detection region being a region at which the detection light beam intersects a plane where the substrate is located when the substrate is moved by the movement device;

a processing unit, configured to determine whether or not the film layer meets a predetermined requirement by determining whether or not an intensity of the photo sensitive signal generated during a period of time where the substrate is moved through the detection region is within a predetermined range, and a sensing device configured to sense whether or not a front end of the substrate has reached the detection region and whether or not a rear end of the substrate has left the detection region, and transmit a sensing signal to the processing unit, wherein the processing unit determines whether or not the film layer meets the predetermined requirement in accordance with the photo sensitive signal during a period of time from the time when the front end of the substrate has reached the detection region to the time when the rear end of the substrate has left the detection region.

13. The system according to claim 12, wherein during the period of time where the substrate is moved through the detection region, when the intensity a of the photo sensitive signal at the detection region always meets $A \leq \alpha \leq B$, the processing unit determines that the film layer meets the predetermined requirement, wherein A represents an intensity of a photo sensitive signal generated when the detection light beam passes through a substrate where a film layer is of a maximum thickness within a predetermined range and distributed evenly, and B represents an intensity of a photo sensitive signal generated when the detection light beam passes through a substrate where a film layer is of a minimum thickness within the predetermined range and distributed evenly; and when $\alpha<A$ or $\alpha>B$, the processing unit determines that the film layer does not meet the predetermined requirement.

14. The system according to claim 13, wherein when $\alpha<A$, the processing unit determines that the thickness of the film layer is of a value greater than the maximum thickness within the predetermined range;

when $B<\alpha<C$, the processing unit determines that the thickness of the film layer is a value less than the minimum thickness within the predetermined range, wherein C represents an intensity of a photo sensitive signal generated when the detection light beam passes through a base substrate where no film layer is arranged; and when $\alpha \geq C$, the processing unit determines that the base substrate includes a region where no film layer is arranged.

15. The system according to claim 12, wherein the light sensor is of a length greater than or equal to the linear light source.

16. The system according to claim 12, wherein the movement device is located between the linear light source and the light sensor.

17. The system according to claim 12, further comprising a collection device connected to the light sensor and the processing unit, and configured to, during the period of time where the substrate is moved through the detection region, collect the photo sensitive signals at a regular time interval and transmit the photo sensitive signals to the processing unit.

18. The system according to claim 12, wherein when the base substrate is made of inorganic glass and the film layer is made of indium tin oxide (ITO), the detection light beam from the linear light source is of a wavelength of 100 nm to 280 nm, or 780 nm to 2526 nm.

19. The system according to claim 12, wherein a side of the base substrate is perpendicular to a movement direction of the movement device and has a length less than or equal to the linear light source.

* * * * *